(12) United States Patent
Matsuo

(10) Patent No.: US 7,044,635 B2
(45) Date of Patent: May 16, 2006

(54) TEMPERATURE CORRECTION METHOD FOR THERMAL ANALYSIS APPARATUS AND THERMAL ANALYSIS APPARATUS

(75) Inventor: Shuichi Matsuo, Tokyo (JP)

(73) Assignee: Rigaku Corporation, Akishima (JP)

( * ) Notice: Subject to any disclaimer, the term of this patent is extended or adjusted under 35 U.S.C. 154(b) by 0 days.

(21) Appl. No.: 10/732,236

(22) Filed: Dec. 11, 2003

(65) Prior Publication Data

US 2004/0120381 A1    Jun. 24, 2004

(30) Foreign Application Priority Data

Dec. 12, 2002  (JP)  ............................. 2002-360289

(51) Int. Cl.
*G01N 25/02*    (2006.01)
(52) U.S. Cl. .............................. 374/10; 374/16; 374/43
(58) Field of Classification Search .................... 374/1, 374/10–13, 14, 16, 30, 179, 208, 43, 183, 374/21, 44, 163; 324/451, 755, 158.1
See application file for complete search history.

(56) References Cited

U.S. PATENT DOCUMENTS

| | | | | |
|---|---|---|---|---|
| 3,456,490 A | * | 7/1969 | Stone | 374/11 |
| 4,320,344 A | * | 3/1982 | Nicholas | 324/451 |
| 5,163,753 A | * | 11/1992 | Whiting et al. | 374/10 |
| 5,211,477 A | * | 5/1993 | Li | 374/33 |
| 5,711,604 A | * | 1/1998 | Nakamura | 374/44 |
| 5,826,983 A | * | 10/1998 | Nakamura et al. | 374/14 |
| 6,007,240 A | * | 12/1999 | Price | 374/55 |
| 6,170,984 B1 | * | 1/2001 | Schawe et al. | 374/10 |
| 6,331,074 B1 | * | 12/2001 | Kimura | 374/10 |
| 6,354,732 B1 | | 3/2002 | Casati et al. | |
| 6,425,686 B1 | * | 7/2002 | Zaldivar et al. | 374/16 |
| 6,551,835 B1 | * | 4/2003 | Schawe et al. | 436/147 |
| 6,676,287 B1 | * | 1/2004 | Mathis et al. | 374/1 |
| 6,791,335 B1 | * | 9/2004 | Hirayama et al. | 324/451 |
| 2002/0024349 A1 | | 2/2002 | Hirayama et al. | |
| 2005/0008061 A1 | * | 1/2005 | Kaneko | 374/16 |
| 2005/0035755 A1 | * | 2/2005 | Schilowitz et al. | 324/158.1 |

FOREIGN PATENT DOCUMENTS

| | | |
|---|---|---|
| JP | 04077654 | 3/1992 |
| JP | 2002-156344 | 5/2002 |

OTHER PUBLICATIONS

Geoffrey A. Bonvalet, "Differential Scanning Calorimetric Study of the Nematic Liquid Crystal 5CB", Physics Department, The College of Wooster, May 6, 1999.

* cited by examiner

*Primary Examiner*—Gail Verbitsky
(74) *Attorney, Agent, or Firm*—Buchanan Ingersoll PC

(57) ABSTRACT

Disclosed is a temperature correction method for a thermal analysis apparatus which measures electric current, voltage, and electric resistance of a measurement sample while changing the temperature of the measurement sample set between a pair of electrodes. The paired electrodes are connected by a reference substance, and a weight is set on the reference substance. The temperature at the time when the reference substance is fused and the weight falls cutting the reference substance is measured actually as melting point by a temperature sensor. Based on a difference between the actually measured value and a literature value of the melting point of the reference substance, the temperature measured by the temperature sensor is corrected. It is thus possible to correct precisely the results measured by the thermal analysis apparatus which deals with electric current, voltage, electric resistance, dielectric constant, electric capacity, thermal electromotive force, thermally stimulated current, and the like, as targets to be measured.

4 Claims, 5 Drawing Sheets

TEMPERATURE CORRECTION METHOD FOR THERMAL ANALYSIS APPARATUS AND THERMAL ANALYSIS APPARATUS

BACKGROUND OF THE INVENTION

1. Field of the Invention

The present invention relates to a thermal analysis apparatus such as a TSC (Thermally Stimulated Current) apparatus, and temperature correction method used for the thermal analysis apparatus.

2. Description of the Related Art

The TSC apparatus mentioned above measures an electric current generated in a sample while changing the temperature of the sample. The TSC apparatus hence has a pair of electrodes which contact the sample, a device which controls the temperature of the sample, and an electric current measurement device which is connected to the pair of electrodes. This TSC apparatus is, for example, disclosed in Japanese Patent Laid-Open Publication No. 2002-156344. This TSC apparatus measures an electric current flowing through a sample in the order of femto ampere ($fA=10^{-15}A$), so that information can be attained concerning the fine structure of the sample, crystal defects, and internal electronic state of the sample. For example, quantitative evaluation can be made with respect to GaAs crystal which is a high-frequency element.

In addition to the TSC apparatus described above, a DSC (Differential Scanning Calorimetry) apparatus and a DTA (Differential Thermal Analysis) apparatus are known as thermal analysis apparatuses.

The DTA is to measure a temperature difference between a sample to be measured and a reference substance while changing the temperatures of both the sample and substance. Found from this measurement are, for example, thermal changes which occur in the sample, e.g., physical changes such as fusion, transition, and the like. The DSC is to measure a calorific difference between a sample to be measured and a reference substance while changing the temperatures of both. The DSC is classified into two known types depending on the difference between their measurement methods, i.e., thermal compensation type DSC and thermal flux type DSC. Physical changes which occur in a sample can also be found by the DSC like case of the DTA.

Both of the DSC and the DTA measure physical characteristics of samples. Temperatures which belong to those physical characteristics such as melting points and the like are known from literature values. Therefore, with respect to the temperature measurement system in an apparatus which practices the DSC or the like, temperature correction can be easily carried by comparing actually measured temperatures with literature values.

In contrast, in the method of measurement, such as the TSC, in which an electric current generated in a sample is directly measured from the sample, physical characteristics of the sample are not measured, and therefore, measured temperatures based on the temperature measurement system which is constituted by using a temperature sensor, thermocouple, etc., cannot be compared with literature values. Consequently, the temperature of the sample measured by the temperature measurement system in the TSC cannot be determined to be correct or not.

SUMMARY OF THE INVENTION

The present invention has been made in view of the above problems and has as its object to realize temperature correction in a measurement system in which electric information concerning a sample, such as electric resistance, a dielectric constant, electric capacity, thermal electromotive force, thermally stimulated current, and the like, is measured by making electrodes directly contact the sample.

A temperature correction method according to the present invention for a thermal analysis apparatus measures a temperature of a sample by a temperature measurement means and measures at least one of electric resistance, dielectric constant, electric capacity, thermal electromotive force, and thermally stimulated current while changing the temperature of the sample, the method comprising:① measuring a melting point of a reference substance while changing a temperature of the reference substance; and ② correcting the temperature measured by the temperature measurement means, based on a difference between the measured melting point of the reference substance and a literature value of the melting point of the reference substance.

The thermal analysis apparatus to be dealt with in the present invention does not have a structure in which physical changes such as fusion, transition, and the like of a sample are measured on the basis of temperature changes of the sample and a reference substance, as in DSC or DTA. However, the thermal analysis apparatus has a structure like a TSC apparatus in which electrodes are made in direct contact with a sample to measure electrical information concerning the sample, e.g., a thermally stimulated current in case of the TSC apparatus. The present invention further includes such thermal analysis apparatuses that measure electric resistance, dielectric constant, electric capacity, thermal electromotive force, and the like.

Known thermal analysis apparatuses of this kind are (a)an EMF (Electro-Motive Force) apparatus which measures electric resistance or thermal electromotive force, (b)an ETA (Electric Thermal Analyzer) which measures resistance, dielectric constant, or electric capacity, (c)a DEA (Dielectric Analysis) apparatus, (d)a DLTS (Deep Level Transient Spectroscopy), (e)an ICTS (Isothermal Capacitance Transient Spectroscopy), (f)a TSIC (Thermally Stimulated Ionic Current) apparatus, and the like, in addition to the TSC apparatus.

Meanwhile, when both ends of two kinds of metal conductors are electrically connected to form a closed circuit and an end of this closed circuit is subjected to heating or the like to give a temperature difference between both ends, an electric current flows through the closed circuit. This phenomenon is known as a so-called Seebeck effect and is applied to thermocouples, for example. The thermal electromotive force mentioned in the present invention is the electromotive force which induces an electric current in the Seebeck effect or the like.

According to the temperature correction method of the present invention, characteristics of a temperature measurement system in the thermal analysis apparatus are investigated by using a reference substance whose melting point, transition temperature, and the like are known objectively. For example, literature values of such a reference substance are internationally approved. Therefore, the results measured by the temperature measurement system can be corrected very precisely.

The temperature correction method constructed as described above may comprise: ① measuring temperatures such as melting points at which plural kinds of reference substances physically change; ② obtaining differences between the measured temperatures of the plural kinds of reference substances and the literature values of physical changes of the reference substances, respectively; ③ obtaining a correction curve by using a least squares method based on the differences between the measured temperatures and the literature values; and ④ correcting temperatures measured by the temperature measurement means based on the correction curves.

When the temperatures at which plural kinds of reference substances physically change are obtained, temperature correction curves are determined precisely. When the temperature correction curves are determined precisely, the measured temperatures can be precisely corrected.

In the temperature correction method constructed as described above, the temperature at which a physical change occurs may be a melting point, transition temperature, or any of other various temperatures. However, the temperature of the physical change should desirably be a melting point. This is because reference substances are easily deformed or cut in their fused states so that the fused states can be easily recognized.

In the above temperature correction method which deals with fusion as the physical change, the electric current flowing through a reference substance should desirably be measured while applying a load to the reference substance. Further, the temperature of the reference substance measured at the time when the measured electric current stops flowing should desirably be determined to be the melting point. This method is very easy, and yet capable of determining the melting point very precisely. Alternatively, a voltage may be applied to the reference substance, and the temperature of the reference substance measured at the time when the applied voltage is not detected any more may be determined to be the melting point.

In the above temperature correction method using a structure in which a load is applied to the reference substance, it is desired that the reference substance be positioned above a hole and a weight be set on the reference substance above the hole, to apply the load. In this case, when the reference substance comes into a fused state, the weight cuts off the reference substance and falls through the hole. Then, the electric current which has been flowing through the reference substance or the applied voltage is not detected any more. As a result, the fused state can be detected correctly. In addition, the structure constituted by the hole and weight is very simple and requires very simple operations at very low costs.

In the temperature correction method as described above, the reference substance should desirably be one or plural substances selected from azoth, indium, tin, zinc, aluminum, silver, and gold. According to the International Temperature Scale 1990 (ITS-90), literature values of melting points of these substances are −38.9° C., 156.6° C., 232.0° C., 419.6° C., 660.4° C., 961.9° C., and 1064.4° C. for azoth, indium, tin, zinc, aluminum, silver, and gold, respectively. Therefore, if three kinds of indium, tin, and zinc are used as reference substances, precise correction curves can be attained within the temperature range of 150 to 400° C. Accordingly, precise temperature correction can be performed within this temperature range.

If gold is selected as a reference substance, temperature correction can be performed within a much higher temperature range. Further, if a substance having a melting point lower than 0° C. like azoth is used as a reference substance, temperature correction is possible within a temperature range not higher than 0° C.

In the temperature correction method as described above, the target to be measured by the thermal analysis apparatus may be an electric current value. For example, considering a TSC apparatus, the electric current value can be measured in the order of femto ampere ($fA=10^{-15}$ A). In case of an apparatus which thus measures an electric current value, a physical change in the reference substance should preferably be detected as a change in the electric current value by a means for measuring the electric current value as a measurement target of the thermal analysis apparatus. In this manner, it is unnecessary to use a dedicated current meter to detect physical changes in the reference substance. Hence, the device for temperature correction can have a simple structure at low costs.

Further, a thermal analysis apparatus, according to the present invention, a) may measures a temperature of a measurement sample by a temperature measurement means and measures at least one of electric resistance, dielectric constant, electric capacity, thermal electromotive force, and thermally stimulated current while changing the temperature of the measurement sample, the device may comprising: b) a pair of electrodes capable of contacting the measurement sample to measure at least one of the electric resistance, dielectric constant, electric capacity, thermal electromotive force, and thermally stimulated current; c) a current measurement means for correcting the measured temperature and being connected to the electrodes; d) a means which controls the temperature of the measurement sample; e) a storage means which stores the temperature measured by the temperature measurement means; f) a reference substance connected between the pair of electrodes; g) a means which applies a load to the reference substance; h) a means which obtains a temperature correction formula based on the measured temperature stored in the storage means; and i) a means which corrects the temperature measured by the temperature measurement means, based on the correction formula.

In the structure as described above, the h) means which obtains a temperature correction formula based on the measured temperature stored in the storage means and the i) means which corrects the temperature measured by the temperature measurement means, based on the correction formula, may be constituted as a function—realization means realized by a computer system comprised of, for example, a CPU (Central Processing Unit), ROM (Read Only Memory), RAM (Random Access Memory), storage medium, and the like. Needless to say, these means may otherwise be realized by a control circuit without using a computer if the control circuit is available for those means.

According to the present invention, characteristics of a sample are investigated by a temperature measurement system in the thermal analysis apparatus, using a reference substance whose melting point, transition temperature, and the like are known objectively. Therefore, the results measured by the temperature measurement system can be corrected very precisely.

In the thermal analysis apparatus constructed as described above, the means which applies a load to the reference substance should desirably have a hole positioned below the reference substance and a weight set on the reference substance above the hole. In this case, when the reference substance comes into a fused state, the weight cuts off the reference substance and falls through the hole. Then, the electric current does not flow though the reference substance any more. As a result, the fused temperature can be detected correctly. In addition, the structure constituted by the hole and weight is very simple and requires very simple operations and also very low costs.

In the thermal analysis apparatus using the temperature correction device constructed as described above, an electric current value may be measured as the target of measurement. To measure the electric current value, a current measurement means may be provided (hereinafter referred to as analysis current measurement means). In this case, the analysis current measurement means should preferably serve also as a current measurement means (hereinafter referred to as correction current measurement means) for detecting that the reference substance physically changes, e.g., the reference substance is fused.

Further, a thermal analysis apparatus according to the present invention comprises the temperature correction device constructed in a structure as described above, and display means which displays measured electric information, e.g., at least one of electric resistance, dielectric constant, electric capacity, thermal electromotive force, and thermally stimulated current. This kind of means may be, for example, a CRT or another type of display, a printer, or the like.

DETAILED DESCRIPTION OF THE PREFERRED EMBODIMENTS

Hereinafter, an embodiment will be described in case of applying the present invention to a TSC apparatus which is a kind of thermal analysis apparatus. Note that the embodiment is an example of the present invention, which is not limited to the embodiment.

Figure 1:
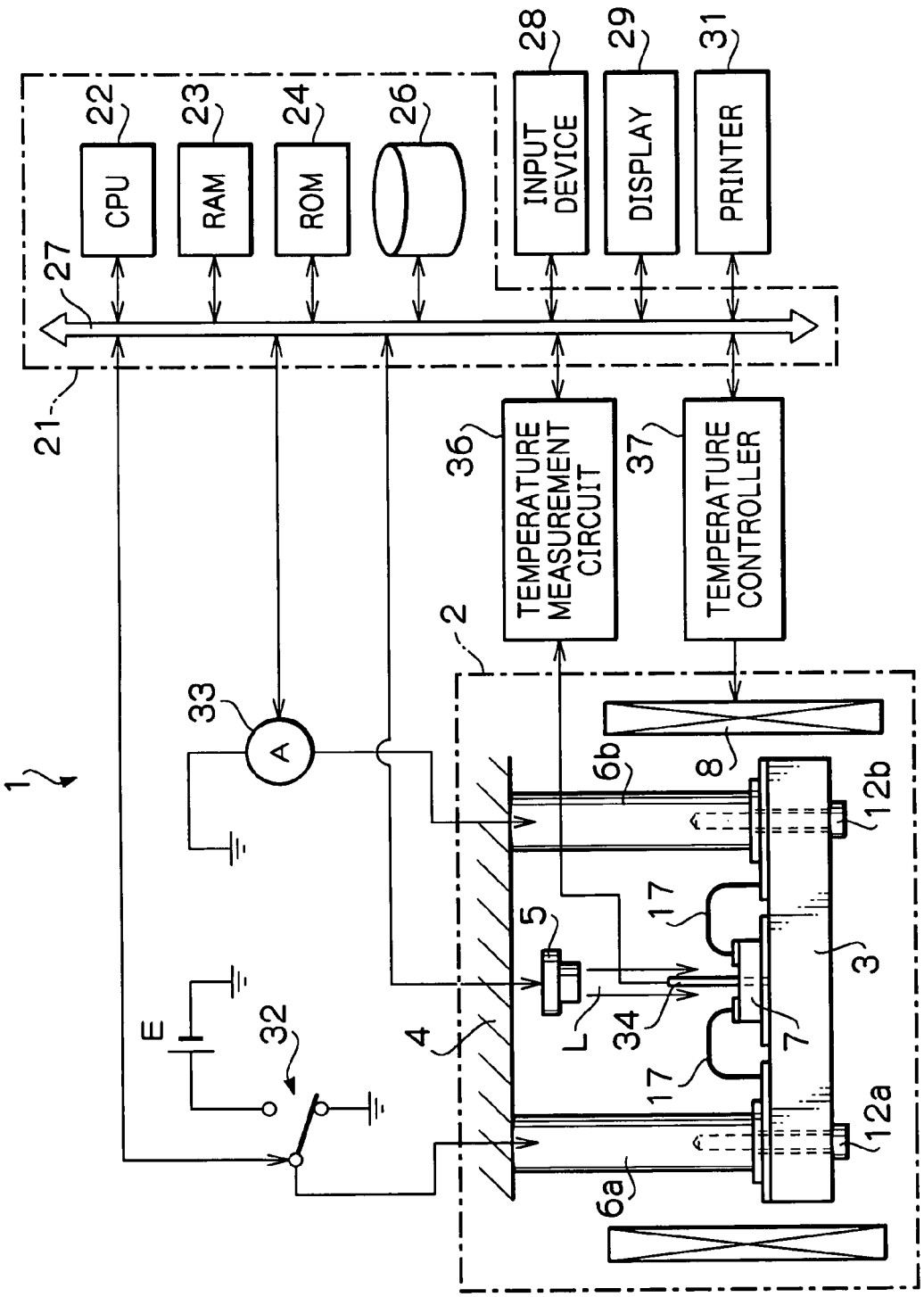
FIG. 1 is a diagram showing an embodiment of a thermal analysis apparatus according to the present invention.

FIG. 1 shows a TSC apparatus as an embodiment of a thermal analysis apparatus according to the present invention. The TSC apparatus 1 has a housing 2, plural (two in the present embodiment) electrode rods 6a and 6b fixed to and suspended from a machine frame 4, a sample support plate 3 which supports a measurement sample 7, a heater 8 which heats the measurement sample 7, and a laser light emission device 5 which emits a laser beam as excitation light to be irradiated on the measurement sample 7. The sample support plate 3 is fixed to lower ends of the electrode rods 6a and 6b by bolts 12a and 12b.

Figure 2A:
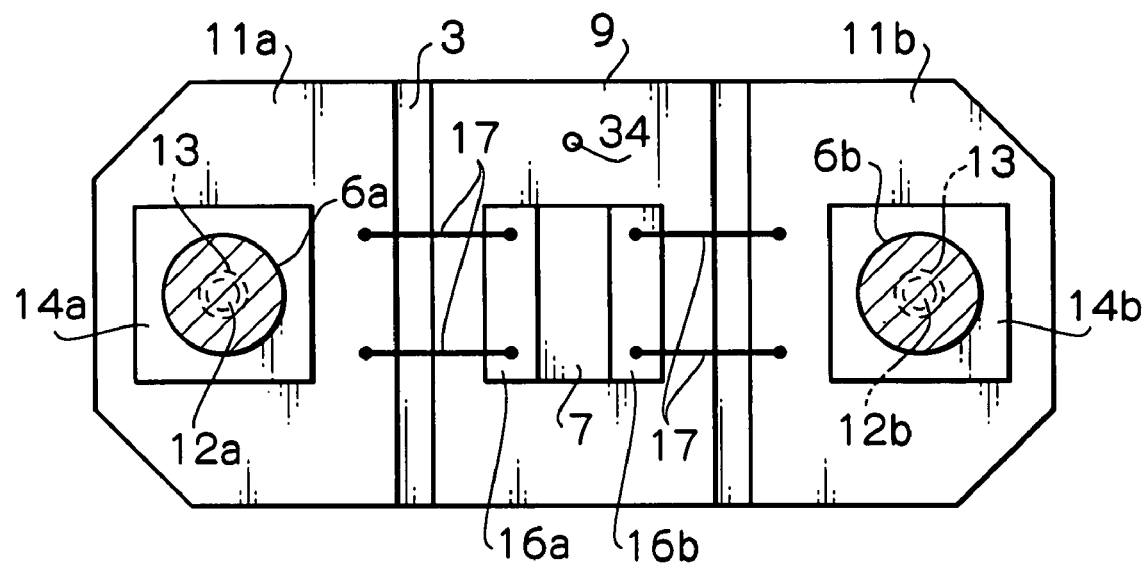
FIG. 2A is a plan view showing a main part of a mechanical part of the thermal analysis apparatus shown in FIG. 1.
Figure 2B:
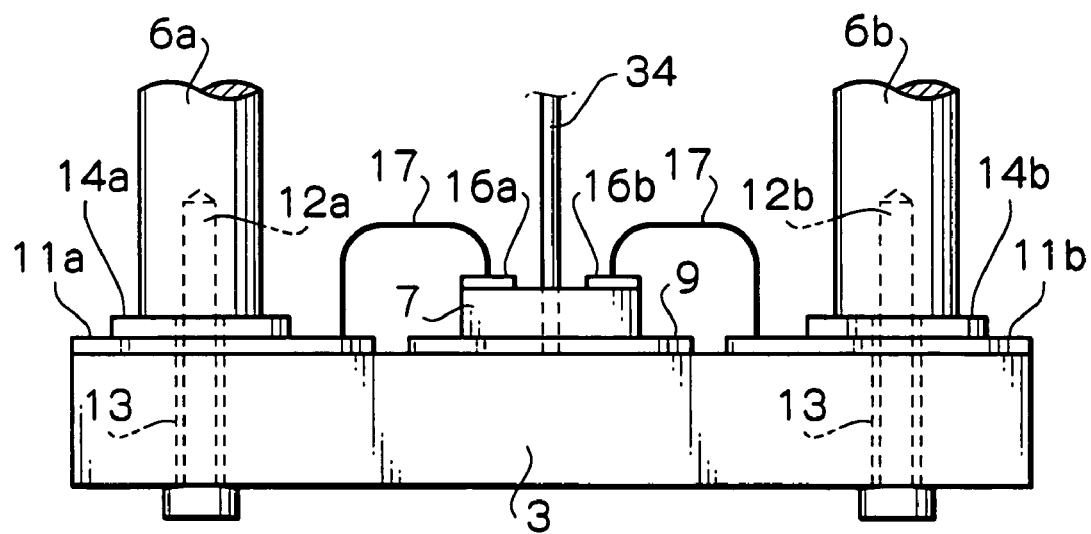
FIG. 2B is a front view showing the main part of the mechanical part of the thermal analysis apparatus shown in FIG. 1.

The sample support plate 3 has a substantially rectangular flat shape whose four corners are cut out, as shown in FIG. 2A. As shown in FIG. 2B, a metal layer 9 is provided on a center part of the sample support plate 3, with relay electrode layers 11a and 11b provided on both end parts of the plate 3 in the lengthwise direction. Clearances are provided between the metal layer 9 and the relay electrode layers 11a and 11b, electrically insulating these layers from each other.

Each of the metal layer 9 and relay electrode layers 11a and 11b is formed in a three-layer structure of Ti/Mo/Au in the order from the side of the sample support plate 3 by a film forming process such as vacuum deposition or the like. Through holes 13 for the bolts 12a and 12b are formed in the areas where the relay electrode layers 11a and 11b are formed, i.e., the parts which are fixed to the electrode rods 6a and 6b.

To fix the sample support plate 3 to the electrode rods 6a and 6b by the bolts 12a and 12b, washers 14a and 14b are inserted between the relay electrode layers 11a and 11b and the bottom surfaces of the electrode rods 6a and 6b, as shown in FIG. 2B. The sample support plate 3 is formed of a material which has excellent thermal conductivity and is electrically insulative, such as aluminum nitride. The washers 14a and 14b are formed of materials which are electrically conductive, such as gold.

The electrode rods 6a and 6b are formed of, for example, stainless steel. These electrode rods 6a and 6b function not only as electrodes during thermal analysis measurement but also as support rods which support the sample support plate 3. In FIGS. 2A and 2B, the top end of a temperature sensor 34 contacts the surface of the metal layer 9 on the sample support plate 3. The temperature sensor 34 may be constituted as follows. For example, a resistor whose resistance value changes depending on changes in temperature, such as platinum resistor, is contained in a tubule made of metal, and a lead connected to a terminal of the resistor is extracted to the outside through the tubule.

The measurement sample 7 is, for example, GaAs crystal and is fixed to the metal layer 9 by an adhesive agent. An adhesive containing mainly Indium can be used as an adhesive of this kind. A pair of electrode layers 16a and 16b are formed on the upper surface of the measurement sample 7 with an interval maintained from each other. These electrode layers are formed, for example, in a three-layer structure of Au/Ni/AuGe layered orderly from the side of the measurement sample 7.

The left electrode layer 16a on the measurement sample 7 is electrically connected to the left relay electrode layer 11a by plural wires 17 made of Au (two wires in the present embodiment). Similarly, the right electrode layer 16b on the measurement sample 7 is electrically connected to the right relay electrode layer 11b by other plural wires 17 also made of Au (two wires in the present embodiment).

In FIG. 1, a control circuit 21 is constituted by a computer which includes a CPU (Central Processing Unit) 22, a RAM (Random Access Memory) 23, a ROM (Read Only Memory) 24, and a storage medium 26. Software for the TSC measurement is stored in a predetermined storage area in the storage medium 26, and the CPU 22 operates in accordance with the software, to execute the TSC measurement.

The control circuit 21 has a bus 27 which is connected to an input device 28, such as a keyboard, a mouse or any other structure via an input/output interface. The bus 27 is also connected to a display 29 which displays information in the form of an image and a printer 31 which records information on a print medium such as a paper sheet or the like. The display 29 and printer 31 each function as a display means to visualize electric current values measured by the TSC apparatus 1.

One electrode rod 6a is grounded or connected to a power source "E" via a switch 32. The switch 32 is connected to the bus 27 via the input/output interface and connects the electrode rod 6a to the ground or power source "E" in accordance with an instruction from the CPU 22. A current measurement device 33 is provided between the other electrode rod 6b and the ground potential. The current measurement device 33 can function to detect an electric current in the order of femto ampere ($fA=10^{-15}A$) and is connected to the CPU 22 and the like via the input/output interface and the bus 27.

Output signals from the temperature sensor 34 are transferred to a temperature measurement circuit 36. This temperature measurement circuit 36 is connected to the CPU 22 and the like via the bus 27. The temperature measurement circuit 36 calculates the temperature of the measurement sample 7, based on the output signal from the temperature sensor 34, and transfers a signal corresponding to the temperature to the control circuit 21. This signal is stored into the RAM 23 or storage medium 26.

The heater 8 for controlling the temperature of the measurement sample 7 is connected to a temperature controller 37. The temperature controller 37 is connected to the CPU 22 via the bus 27, and drives the heater 8 in accordance with an instruction from the CPU 22. Considering decrease in the temperature of the measurement sample 7, for example, a structure for supplying a cooling medium such as liquid nitrogen may be provided in the housing 2.

Next description will be made of TSC measurement which is carried out by a thermal analysis apparatus constructed in the structure as described above, using GaAs crystal as the measurement sample 7. At first, the measurement sample 7 is cooled to a low temperature of $-180°$ C. or so. Then, a laser beam having a specific wavelength is generated as excitation light, to irradiate the measurement sample 7 with the laser beam from upside.

Next, the temperature of the measurement sample 7 is raised by the heater 8. During the increase of the temperature, carriers are discharged from crystal defects of the measurement sample 7, so that a very weak electric current induced from the discharged carriers is generated at about $10^{-13}A$ to $10^{-15}A$. This weak electric current is measured by the current measurement device 33, and thus, the internal crystal defects of the measurement sample 7 can be analyzed. Note that the switch 32 in FIG. 1 is switched to the grounded side or the power source "E" side in accordance with the type of measurement sample 7 or the type of measurement to be carried out.

As long as the TSC apparatus 1 is concerned, the temperature of the measurement sample 7 is measured by a temperature measurement system using the temperature sensor 34. However, this temperature measurement system may be considered to involve variants in the measured results, depending on variants in the characteristics of the temperature sensor 34 and other elements. Correct temperatures hence cannot always be measured.

To eliminate this drawback, the TSC apparatus 1 according to the present embodiment performs the following temperature correction process in order that the temperature measured by the temperature measurement system be accurate. The temperature correction process may be carried out every time when the TSC measurement is carried out or periodically at a predetermined time interval.

(Temperature Correction Process)

Figure 3A:
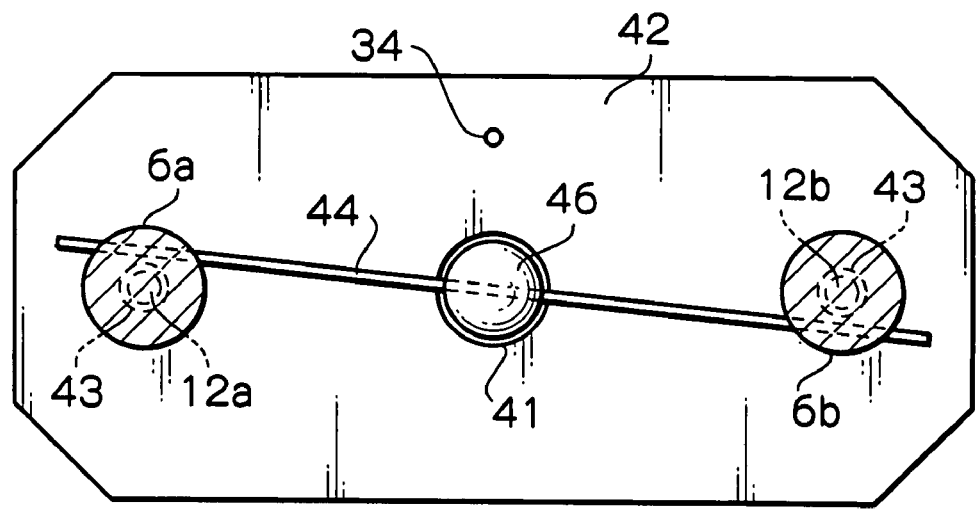
FIG. 3A is a plan view in case where the thermal analysis apparatus shown in FIG. 1 is used as a temperature correction device.
Figure 3B:
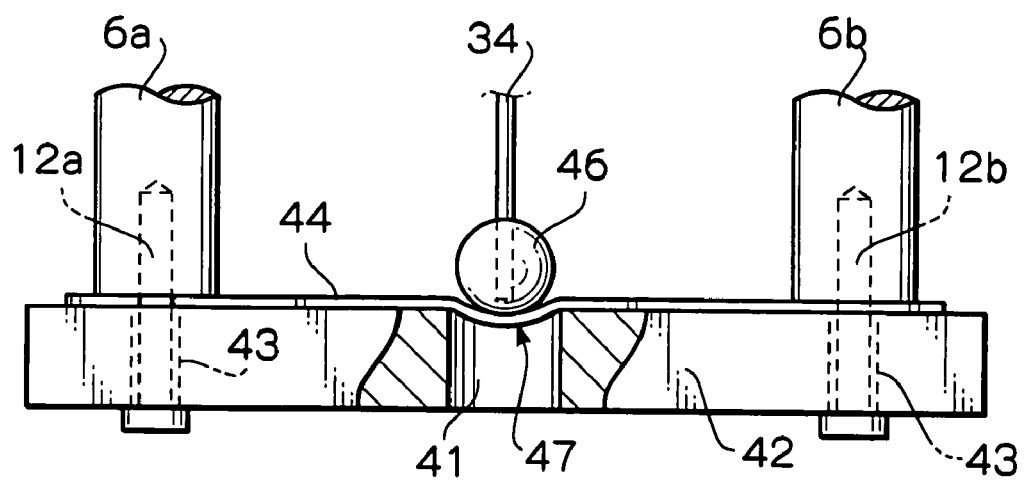
FIG. 3B is a front view in case where the thermal analysis apparatus shown in FIG. 1 is used as the temperature correction device.

Firstly, in FIG. 2B, the bolts 12a and 12b are loosened, and the sample support plate 3 is detached from the electrode rods 6a and 6b. Meanwhile, as shown in FIGS. 3A and 3B, a support plate 42 is prepared, with a through hole 41 formed in the center part of the plate 42 and holes 43 formed in both end parts thereof to pass the bolts. The support plate 42 is made of material which has excellent thermal conductivity and is electrically insulative.

Plural kinds, for example, three kinds of strip-like reference substances 44 are also prepared. In the present embodiment, the prepared three kinds of reference substances are indium, tin, and zinc. Further, one of the three kinds of strip-like reference substances 44 is set on the surface of the support plate 42, crossing the through hole 41 and extending near the holes 43 for passing the bolts. In this case, indium is selected as the first one from the three kinds of reference substances.

Next, the bolts 12a and 12b are let penetrate the through holes 43 of the support plate 42, and further screwed into the electrode rods 6a and 6b, thus fixing the support plate 42 to the bottom surfaces of the electrode rods 6a and 6b. In this case, both end parts of the reference substance 44 are respectively sandwiched between the support plate 42 and the bottoms surfaces of the electrode rods 6a and 6b. In this manner, the both ends of the reference substance 44 are electrically connected to the electrode rods 6a and 6b. Note that electrically conductive washers may be inserted between the reference substance 44 and the electrode rods 6a and 6b in order to stabilize contacts between the reference substance 44 and the electrode rods 6a and 6b.

Next, a weight (i.e., mass) 46 is set on the reference substance 44 crossing the through hole 41. To stabilize the weight 46, a concave 47 may be desirably formed in advance in the reference substance 44 at the part where the weight 46 is set, as shown in FIG. 3B. The weight 46 may be formed of, for example, stainless steel. By thus setting the weight 46 on the reference substance 44 at the position of the hole 41, a load i.e., force) can be applied to the reference substance 44. When the reference substance 44 is set at a room temperature, the weight 46 is supported on the reference substance 44 by mechanical strength thereof.

Figure 4A:
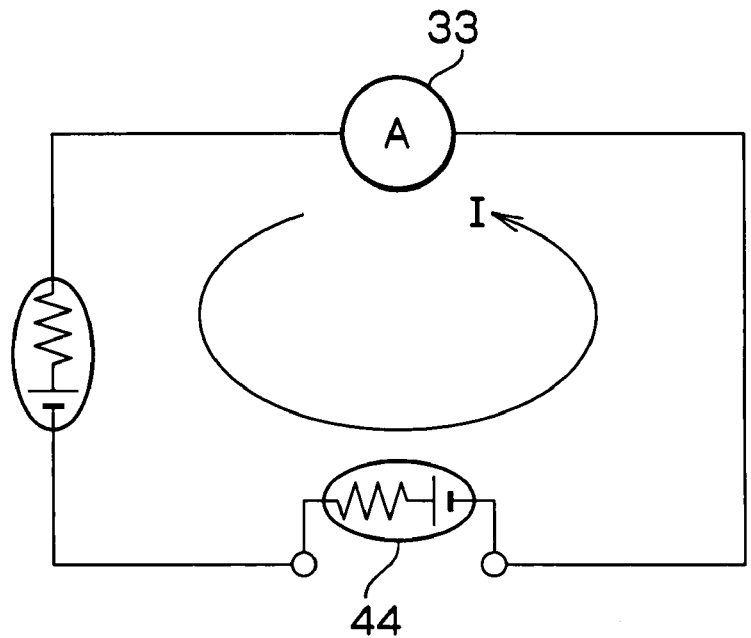
FIG. 4A is an electric equivalent circuit diagram of the device shown in FIGS. 3A and 3B where no voltage is applied.
Figure 5:
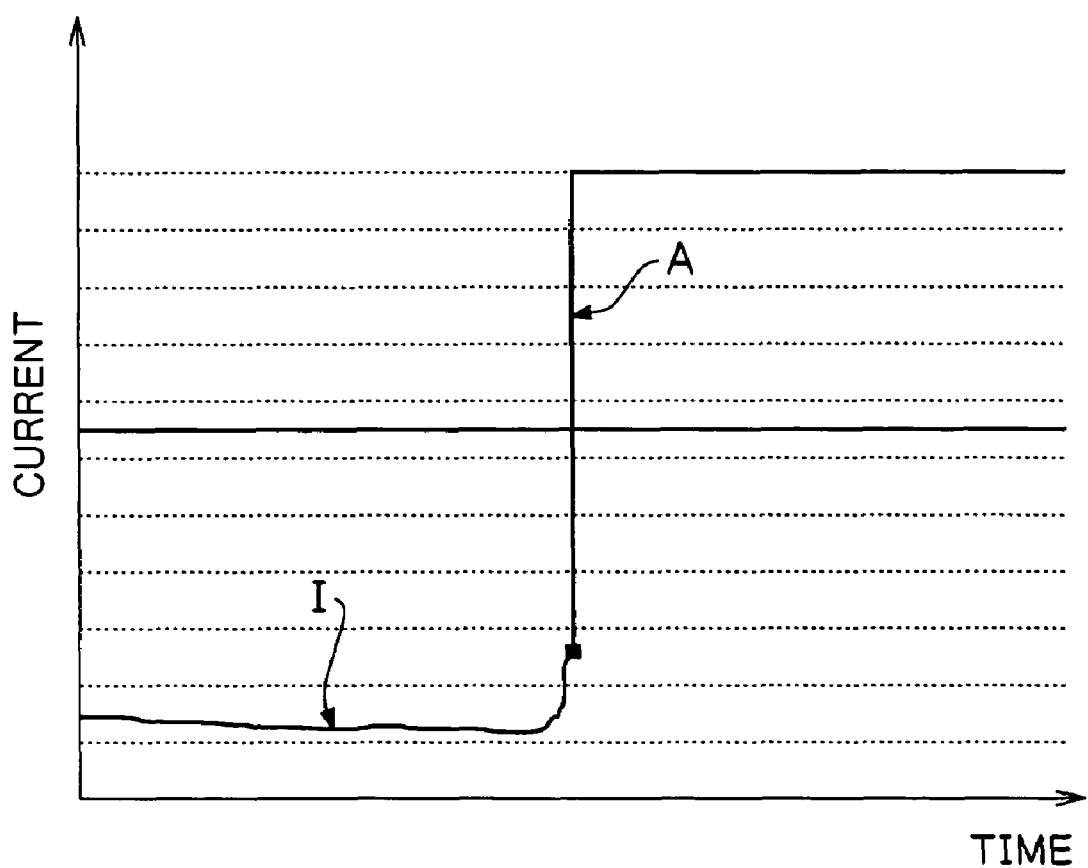
FIG. 5 is a graph showing changes in electric current in case where the melting point of a reference substance is detected by the device shown in FIGS. 3A and 3B.

Suppose now that the switch 32 shown in FIG. 1 is set to the grounded side. The circuit constituted by the electrode rods 6a and 6b, the support plate 42, and the like shown in FIG. 3B is then considered to be an equivalent circuit as shown in FIG. 4A. In this circuit, an electric current "I" flows through the circuit due to the battery effect, Seebeck effect, electromagnetic induction, electrostatic induction, and the like. The current measurement device 33 measures the electric current "I" as indicated by the reference symbol "I" in FIG. 5.

Next, the reference substance 44 is heated by the heater 8 (see FIG. 1) to increase the temperature thereof. When the temperature reaches the melting point of indium which forms the reference substance 44, i.e., $156.6°$ C., the reference substance melts, and the weight 46 which has been set on the reference substance 44 drops cutting the reference substance 44 through the hole 41. As the reference substance 44 is thus cut, the electric current "I" which has been flowing through the circuit shown in FIG. 4A does not flow any more, as indicated at the reference symbol A in FIG. 5. Therefore, the CPU 22 in FIG. 1 determines at this time point that indium as the reference substance 44 reaches its own melting point.

The CPU 22 then stores the temperature of the reference substance 44 measured at this time point by the temperature measurement circuit 36, as the melting point, into the RAM 23 or the storage medium 26. In this manner, the melting point of indium is measured by the temperature measurement system including the temperature sensor 34 and the temperature measurement circuit 36. Subsequently, the same process as described above is repeated for the remaining two of the three kinds of reference substances 44, i.e., tin and zinc. As a result, the melting points of tin and zinc are measured by the temperature measurement system including the temperature sensor 34 and the temperature measurement circuit 36.

While actually measured values of melting points are thus attained with respect to the three kinds of reference substances 44, the operator of the measurement inputs literature values of melting point which are internationally approved for the three kinds of reference substances 44, e.g., values disclosed in International Temperature Scale 1990 (ITS-90), via the input device 28 shown in FIG. 1. The literature values thus inputted are stored into a predetermined storage area in the RAM 23 or storage medium 26. Note that the inputting by the operator of the measurement need not always be waited but data of those literature values concerning melting points may be previously stored in the software stored in the storage medium 26 or in the form of a special data table stored in the storage medium 26.

Thus, the actually measured values and literature values concerning the melting points of the three kinds of substances of indium, tin, and zinc are stored into a predetermined storage area in the control circuit 21. The CPU 22 then calculates the differences between the actually measured values and the literature values. Based on the temperature difference data, A, B, and C in the following quadratic equation (1) for correction are determined according to a least squares method.

$$T = At^2 + Bt + C \quad (1)$$

The capital "T" is the true temperature to be attained, i.e., the temperature after correction, and the lowercase "t" is a measured temperature (i.e., coefficient A, B, C are determined by substitution known value of the melting point temperatures of the reference substances into "T" and substituting measured melting point temperature of the reference substance in "t". The correction formula expressed above by the equation (1) is stored in a predetermined storage area in the RAM 23 or the storage medium 26.

If the correction equation (1) is thus stored in the control circuit 21, the temperature value is corrected on the basis of the above equation (1) when a temperature value is measured with respect to the measurement sample 7 by the temperature sensor 34 and the temperature measurement circuit 36, as explained in relation to the TSC apparatus 1 shown in FIG. 1. More specifically, for example, "t" in the equation (1) is substituted with a measured value of the temperature to determine the true temperature value "T". As a result, correct temperatures can be measured in the TSC measurement. An electric current value of the measurement sample 7 which corresponds to the corrected true temperature is measured by the current measurement device 33.

In the present embodiment, indium, tin, and zinc are used as the reference substances 44. The melting points of these substances are 156.6° C., 232.0° C., and 419.6° C. for indium, tin, and zinc, respectively. If the above temperature correction formula (1) is solved by these temperatures, the correction formula can be applicable to the temperature range of 156.6 to 419.6° C. or a slightly wider temperature range in practice, e.g., the temperature range of 150 to 400° C. If another substance than the foregoing three kinds are considered as the reference substance 44, there can be provided a correction formula capable of correcting a temperature out of the temperature ranges described above. For example, if gold (Au) having a melting point of 1064.4° C. is used, correction is possible within a much higher temperature range. Alternatively, if azoth (Hg) having a melting point of −38.9° C. is used, correction is possible within a temperature range of 0° C. or lower.

(Modifications)

Figure 4B:
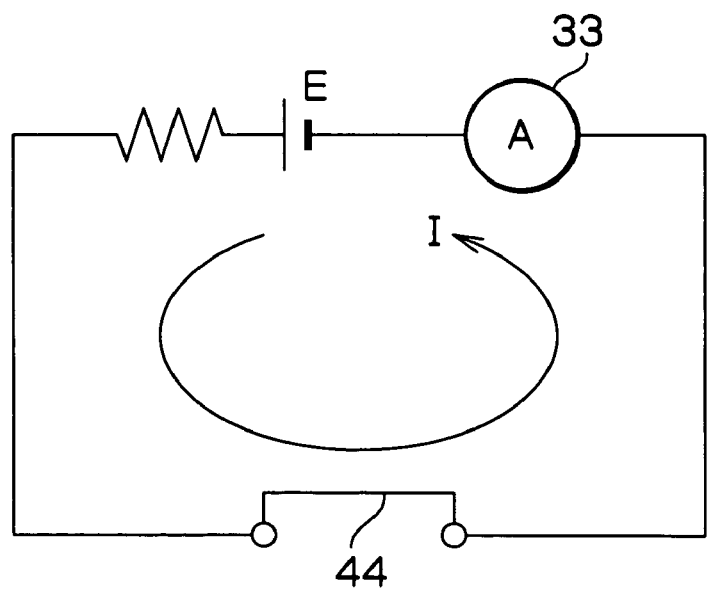
FIG. 4B is an electric equivalent circuit diagram of the device shown in FIGS. 3A and 3B where a voltage is applied.

In the above description, the switch 32 shown in FIG. 1 is set to the grounded side in the temperature correction device shown in FIGS. 3A and 3B, to constitute a correction circuit as shown in FIG. 4A. Alternatively, if the switch 32 is set to the power source "E" side in FIG. 1, a correction circuit can be constituted as shown in FIG. 4B. In this circuit, changes in the electric current "I" flowing through the circuit in accordance with the power source voltage "E" are detected by the current measurement device 33.

Also in the description made above, the current measurement device 33 which is originally used to perform TSC measurement is also used as a current meter to detect the melting point of the reference substance 44 such as indium, tin, zinc, or the like. A current meter for detecting the melting point may be provided separately from the current measurement device for the TSC measurement.

Also in the above description, a TSC apparatus has been supposed to measure the thermally stimulated current as a measurement target. In addition to the TSC apparatus, however, other various thermal analysis apparatuses based on EMF, ETA, and the like may be considered as thermal analysis apparatuses to which the present invention is applicable. Also, the measurement target is not limited to the thermally stimulated current but may be electric resistance, dielectric constant, electric capacity, thermal electromotive force, or the like.

The above embodiment deals with the very weak electric current flowing through the measurement sample 7, as a measurement target. The present invention is also applicable to such a thermal analysis apparatus which deals with other electric information than the electric current, as a measurement target, e.g., the resistance value of the sample, the voltage applied to the sample, or the like.

In the TSC apparatus 1 shown in FIG. 1, GaAs crystal is the measurement sample 7. This measurement sample necessitates irradiation on the measurement sample 7 with excitation light such as a laser beam. In contrast, there is a case that a substance such as a plastic film which requires no irradiation of the laser beam but necessitates clamping of the sample itself from both of the top and bottom sides by electrodes is measured by the TSC apparatus 1. In this case, the sample support plate in FIG. 1 may be appropriately modified or a mechanism which enables a pair of upper and lower electrodes to clamp the sample may be added. Measurement on such a plastic film can thus be achieved. Japanese Patent Application Laid-Open Publication No. 2002-156344 discloses the details of this measurement.

What is claimed is:

1. A temperature correction method for a thermal analysis apparatus, which measures a temperature of a measurement sample by temperature measurement means and measures at least one of electric resistance, dielectric constant, electric capacity, thermal electromotive force, and thermally stimulated electric current while changing the temperature of the measurement sample, the method comprising the steps of:

measuring temperature of a measurement sample by the temperature measurement means;

measuring a melting point temperature of a reference substance while changing a temperature of the reference substance;

measuring an electric current flowing through the reference substance or a voltage applied to the reference substance while applying a load force to the reference substance;

determining the temperature of the reference substance measured at the time when the measured electric current does not flow any more or the applied voltage is not detected any more to be a melting point; and correcting the temperature measured by the temperature measurement means, based on a difference between the measured melting point temperature of the reference substance and a known value of the melting point temperature of the reference substance.

2. The method according to claim 1, wherein the reference substance is positioned on a hole for receiving the load force, and a weight is set on the reference substance above the hole, the weight serving as the load force applied to the reference substance.

3. A thermal analysis apparatus, which measures a temperature of a measurement sample by temperature measurement means the apparatus is capable of measuring at least one of electric resistance, dielectric constant, electric capacity, thermal electromotive force, and thermally stimulated current while changing the temperature of the measurement sample, the apparatus comprising:

a temperature measurement means;

a pair of electrodes contacting the measurement sample capable of measuring at least one of the electric resistance, dielectric constant, electric capacity, thermal electromotive force, and thermally stimulated current while changing the temperature of the measurement sample;

means which controls the temperature of the measurement sample measured by the temperature measurement means;

storage means which stores the temperature measured by the temperature measurement means;

a reference substance connected between the pair of electrodes;

means which applies a load force to the reference substance to determine the temperature of the reference substance to be a melting point;

means which obtains a temperature correction formula based on the measured temperature stored in the storage means and the melting point of the reference sample; and means for using the temperature measured by the temperature measurement means, based on the temperature correction formula for controlling a current measurement means used for correcting the measured temperature and being connected to said pair of electrodes.

4. The thermal analysis apparatus according to claim 3, wherein the means which applies the load force to the reference substance has a hole positioned below the reference substance and a weight set on the reference substance.

* * * * *